United States Patent [19]

McLean et al.

[11] Patent Number: 4,527,979
[45] Date of Patent: Jul. 9, 1985

[54] POWDERED DENTAL MATERIAL AND PROCESS FOR THE PREPARATION THEREOF

[75] Inventors: John W. McLean, London, England; Oswald Gasser, Seefeld, Fed. Rep. of Germany

[73] Assignee: ESPE, Fabrik pharmazeutischer Präparate GmbH, Seefeld, Fed. Rep. of Germany

[21] Appl. No.: 563,749

[22] Filed: Dec. 21, 1983

[30] Foreign Application Priority Data

Dec. 28, 1982 [DE] Fed. Rep. of Germany ....... 3248357

[51] Int. Cl.$^3$ ................................................ A61K 6/08
[52] U.S. Cl. ..................................... 433/228; 106/35; 260/998.11; 433/9; 433/226; 523/115; 523/116; 523/117; 523/118
[58] Field of Search ..................... 260/998.11; 106/35; 523/115, 116, 117, 118; 433/228, 9, 226

[56] References Cited

U.S. PATENT DOCUMENTS 3,814,717 6/1974 Wilson ............................ 260/998.11
4,209,434 6/1980 Wilson et al. ........................ 106/35
4,376,835 3/1983 Schmitt et al. ....................... 106/35

FOREIGN PATENT DOCUMENTS 2028855 3/1980 United Kingdom .

Primary Examiner—Lorenzo B. Hayes
Attorney, Agent, or Firm—Birch, Stewart, Kolasch & Birch

[57] ABSTRACT

Powdered dental material of a sintered mixture of calcium aluminum fluorosilicate glass and precious metals (or alloys thereof with each other or with up to 40% non-precious metals), which may optionally contain polycarboxylic acid and/or a chelating agent and/or further powdered precious metal. The dental material can be prepared by sintering a mixture of the glass and the precious metal at a temperature greater than 600° C., grinding the sintered product to a powder and admixing the optional further components. Use of the self-hardening glass ionomer cements for dental filling purposes gives fillings having excellent resistance to wear, most notably at the edges and corners in the molar region.

19 Claims, No Drawings

POWDERED DENTAL MATERIAL AND PROCESS FOR THE PREPARATION THEREOF

The invention relates to a powdered dental material, its preparation and its use.

Glass ionomer cements constituting the reaction product of a calcium aluminum fluorosilicate glass powder, a water-soluble polycarboxylic acid and water offer the advantage over other dental materials used for filling purposes (e.g., composite plastic fillings and amalgams) of being biologically compatible and of chemically bonding to the tooth substance so that they provide a perfect marginal seal. The disadvantage of the glass ionomer cements resides in their relatively high brittleness which has hitherto precluded the use thereof in the molar region and at corners and edges.

Metal-containing glass ionomer cement powders are disclosed in British Pat. No. 2,028,855. However, these are mere mixtures of cement powder and metal powder which have not been subjected to thermal treatment. The wear resistance of these mixtures tends to be inferior to that of pure glass ionomer cements.

West German patent application (OLS) No. 30 42 008, laid open for public inspection, teaches a tooth filling material which consists of a matrix-like metallic component with open voids and a non-metallic component, e.g., a glass ionomer cement, as a liquid or plastic material. For the production thereof the matrix-like metallic component is either wetted or impregnated with the non-metallic component, or the matrix-like metallic component is kneaded into the non-metallic component. The matrix-like metallic component may be produced by sintering metal powders. In this tooth filling material also, the metallic component is only mixed, for example, with the glass ionomer cement without having been previously sintered with a calcium aluminum fluorosilicate glass.

It is an object of the present invention to provide a powdered dental material on the basis of a glass ionomer cement powder which exhibits better wear resistance than that of a pure glass ionomer cement.

According to the invention, this object is realized by the provision of a powdered dental material comprising (a) calcium aluminum fluorosilicate glass, (b) precious metals customarily used for dental purposes or the alloys thereof with one another and/or with up to 40% by weight of non-precious metals, based on the weight of the alloy, and, optionally, (c) at least one dry polycarboxylic acid and/or chelating agent, which contains at least a portion of the component (a) in the form of a sintered mixture with the component (b).

According to the invention, the novel powdered dental material is produced by mixing a powder of (a) calcium aluminum fluorosilicate glass and (b) of precious metals customarily used for dental purposes such as gold or silver or the alloys thereof with one another and/or with up to 40% by weight of non-precious metals, based on the weight of the alloy, sintering the resulting mixture at a temperature in excess of 600° C., optionally after molding it into a shaped structure, and grinding the sintered product to form a powder. The resulting sintered product may optionally be blended with (1) unsintered calcium aluminum fluorosilicate glass and/or (2) with dry polycarboxylic acid and/or (3) with a chelating agent, each in powdered form.

For use, the powdered dental material of the invention, in case (1), is mixed with an aqueous polycarboxylic acid solution optionally containing a chelating agent; in case (2) it is mixed with water optionally containing a chelating agent, e.g., tartaric acid; and in case (3) it is mixed with aqueous polycarboxylic acid or with water to form a tooth filling material which exhibits high resistance to wear so that it is suited also for forming edges and corners in the molar region. The cement prepared from the dental material of the invention adheres to the tooth substance and is physiologically and biologically compatible.

Calcium aluminum fluorosilicate glass powders useful for the dental material of the invention have been described in, for example, U.S. Pat. Nos. 3,814,717 and 4,376,835.

The calcium aluminum fluorosilicate glass powders employed according to the invention preferably consist of the following components, in addition to oxygen:

| Component | Calculated as | % by Weight |
|---|---|---|
| Si | $SiO_2$ | 20 to 60 |
| Al | $Al_2O_3$ | 10 to 50 |
| Ca | CaO | 1 to 40 |
| F | F | 1 to 40 |
| Na | $Na_2O$ | 0 to 10 |
| P | $P_2O_5$ | 0 to 10 | and altogether 0 to 20% by weight, calculated as oxides, of B, Bi, Zn, Mg, Sn, Ti, Zr, La or other trivalent elements of the lanthanide series, K, W, Ge and further additives which do not impair the properties thereof and which are biologically unobjectionable.

Preferably the powder particles consist of

| | |
|---|---|
| Si as $SiO_2$ | 25 to 50% by weight |
| Al as $Al_2O_3$ | 10 to 40% by weight |
| Ca as CaO | 10 to 35% by weight |
| F | 5 to 30% by weight |
| Na as $Na_2O$ | 0 to 8% by weight |
| P as $P_2O_5$ | 1 to 10% by weight | and 0 and 10% by weight of $B_2O_3$, $Bi_2O_3$, ZnO, MgO, $SnO_2$, $TiO_2$, $ZrO_2$, $La_2O_3$ or other oxides of trivalent elements of the lanthanide series, $K_2O$, $WO_3$, $GeO_2$, and further additives which do not impair the properties thereof and which are biologically unobjectionable.

Especially preferred powders contain

| | |
|---|---|
| Si as $SiO_2$ | 25 to 45% by weight |
| Al as $Al_2O_3$ | 20 to 40% by weight |
| Ca as CaO | 10 to 30% by weight |
| F | 10 to 30% by weight |
| Na as $Na_2O$ | 1 to 8% by weight |
| P as $P_2O_5$ | 1 to 10% by weight |

Examples of the preferably used compositions are compiled in the following Table I.

TABLE I

| | Percent by Weight | | | |
|---|---|---|---|---|
| | A | B | C | D |
| Si as $SiO_2$ | 35.0 | 27.6 | 29.0 | 45.4 |
| Al as $Al_2O_3$ | 30.4 | 26.0 | 25.1 | 35.0 |
| Ca as CaO | 14.9 | 28.8 | 24.6 | 10.1 |
| F | 17.7 | 17.0 | 23.0 | 10.4 |
| Na as $Na_2O$ | 2.7 | 2.1 | 2.2 | 6.9 |
| P as $P_2O_5$ | 6.9 | 8.3 | 5.8 | 2.4 |

The glass powder particles used according to the invention may be depleted in calcium at the surface so that the quotient of the atomic ratio Si/Ca at the powder particle surface and the atomic ratio Si/Ca in the core region is at least 2.0, preferably at least 3.0, and most preferably at least 4.0 (see U.S. Pat. No. 4,376,835). These powders are used especially advantageously as an admixture to the ground metal-containing sintered product.

The glass powders employed according to the invention have an average particle size (weight average) of at least 1 micron and preferably at least 3 microns. The average particle size (weight average) ranges from 1 to 20 microns, preferably 3 to 15 microns, and most preferably 3 to 10 microns. The particles have a maximum particle size of 150 microns, preferably 100 microns, especially 60 microns. For use as a fixing cement, the maximum particle size is 25 microns, preferably 20 microns. In order to obtain good mechanical properties it is favorable to have a particle size distribution that is not too narrow, as usual, and which is attained, for example, by conventional grinding and screening off of coarser fractions.

As usual, the glass powders are obtained by co-melting the starting components at temperatures above 950° C., quenching and grinding. The compounds disclosed, for example, in U.S. Pat. No. 3,814,717 may be employed in suitable quantitative ranges as the starting materials.

The thus obtained powders are then optionally subjected to a surface treatment as described in U.S. Pat. No. 4,376,835. To this end the glass powders are subjected to a surface treatment with acid, preferably at room temperature. For this treatment substances containing acidic groups are employed, e.g., hydrochloric acid, sulfuric acid, nitric acid, acetic acid, propionic acid or perchloric acid, which form soluble calcium salts. The acids are used at a concentration from 0.01 to 10% by weight, preferably from 0.05 to 3% by weight.

After an adequate reaction period the powders are separated from the solution and thoroughly rinsed so that substantially no soluble calcium salts remain on the surface of the powder particles. The powder particles depleted in calcium on the surface are especially well suited for admixture with the ground metal-containing sintered products.

For use as precious metal powder, the precious metals customarily known and used in dentistry such as gold, platinum, palladium and silver are suitable, as well as the alloys thereof with one another and with up to 40% by weight of non-precious metals, based on the alloy weight, such as copper, tin, indium, and zinc. An example of an alloy useful in the present invention is an alloy composed of 65% by weight of silver and 35% by weight of tin. Silver and gold are the preferred precious metals, as well as the alloys thereof with not more than 10% by weight of other metals.

The average particle size (weight average) of the precious metal powder component (b) is at least 0.5 micron, preferably at least 1 micron, and most preferably at least 3 microns. Th weight average of the particle size distribution is preferably between 0.5 and 20 microns, especially between 1 and 10 microns. The maximum particle size of the metal powders should not exceed 60 microns, preferably 40 microns, and especially 10 microns. Preferably at least 90% of the particles of the precious metal powder component (b) have a particle size less than 32 microns, most preferably less than 10 microns.

The powdered dental material of the invention may also contain dry polycarboxylic acid. For this purpose, the polycarboxylic acids known for the production of glass ionomer cement powders may be employed, e.g., polymaleic acid, polyacrylic acid and mixtures thereof, or copolymers, especially maleic acid/acrylic acid copolymers and/or acrylic acid/itaconic acid copolymers.

Moreover, the dental material of the invention may contain a chelating agent (cf. U.S. Pat. No. 4,209,434). The preferred chelating agent is tartaric acid.

In order to carry out the process of the invention, first the powdered glass component (a) and the powdered precious metal component (b) are mixed. The proportion of the precious metal component (b) in the mixture of (a) and (b) may range from 20 to 80, preferably from 40 to 60% by volume of the mixture of (a)+(b).

The glass/metal powder mixture may be sintered directly. Thus, for instance, moldings may be produced in a pelletizer. Pelletizing is preferably carried out at high pressures, e.g., in a hydraulic press, especially at pressures above 3000 kg/cm$^2$. It is favorable to evacuate the pelleting chamber during the pelletizing operation, e.g., to a pressure of less than 10 mbar.

The powder mixture or the pellets made therefrom are sintered at temperatures above 600° C. Sintering preferably is effected in a vacuum, especially below 10 mbar, and most preferably below 5 mbar. The sintering temperature is maintained preferably below the melting point of the precious metal component (b) employed; if the precious metal component consists of silver or gold, a sintering temperature of about 800° C. is suitably employed. The sintering period may range from a few minutes to several hours, for example, from 10 minutes to 3 hours for pellets, depending on the size thereof. Before the sintered product is removed from the annealing furnace, it is favorable to allow it to cool to a temperature below 600° C.

The resulting sintered structures are ground to a fine powder in the usual way. The average particle size (weight average) and the maximum particle size of the powdered dental material are the same as those described above for the calcium aluminum fluorosilicate powder to be subjected to sintering.

The resulting powder may also be mixed with the above described unsintered calcium aluminum fluorosilicate glass powder. Preferably 10 to 50% by volume of unsintered calcium aluminum fluorosilicate glass powder are added, based on the sintered product. Powders depleted in calcium on the surface are especially suited for this purpose.

The ground sintered product or the mixture thereof with unsintered glass powder may also be mixed with dry, finely particulate polycarboxylic acid at a weight ratio of 1:1 to 5:1. Moreover, a chelating agent in powdered form may be added to any one of these mixtures.

The powdered dental materials of the invention are used in the manner customary for glass ionomer cement powders. In case the dental material of the invention does not contain dry polycarboxylic acid, it is mixed at a weight ratio from 2:1 to 10:1, preferably 4:1 to 8:1, with an aqueous polycarboxylic acid solution in which optionally a chelating agent, e.g., tartaric acid, is dissolved. For this purpose the same polycarboxylic acids, in the form of their aqueous solutions, as those which may be mixed in finely divided dry form with the metal-containing powder of the invention are suitably employed. If the dental material of the invention already contains dry polycarboxylic acid, the dental material is mixed with water, optionally with the addition of a chelating agent, to acquire a cement-like consistency.

Tooth filling cements prepared with the powdered dental material of the invention give tooth fillings which have excellent resistance to wear, notably at the edges and corners in the molar region, while tooth fillings of glass ionomer cements without metal content or merely with admixed metal content are subject to relatively rapid decay due to edge breakage and high abrasion.

In addition to filling purposes in the molar region, the dental materials of the invention may be used also for the usual fillings if they are not in the directly visible area of the teeth. Furthermore, the material of the invention can be used for building up destroyed stumps prior to crowning. If the maximum particle size of the material does not exceed 20 microns, the dental material of the invention is suited also for use as fixing cement, e.g., for crowns and bridges.

Primarily with the use of gray metals, such as silver, the color of the filling material can be improved by the addition of up to 5% of a white or yellow pigment (e.g., titanium dioxide or zinc oxide). In this way, the material is also suitable for filling purposes in the front region on the lingual side of the teeth.

The following Examples are given merely as illustrative of the present invention and are not to be considered as limiting.

EXAMPLE 1

Gold-Containing Sintered Powder

A calcium aluminum fluorosilicate glass powder of the composition A in Table I (average particle size, 8 microns) is intimately blended at a volume ratio of 1:1 with a fine gold powder (99% gold, all particles smaller than 5 microns) and molded into cylindrical pellets of 13 mm diameter and 5 mm height at a pressure of 7000 kg/cm$^2$ under a vacuum of 4 mbar.

The pellets are heated in a vacuum of 4 mbar and at a temperature of 800° C. for 1 hour. After the furnace has cooled down to a temperature below 600° C., the pellets are removed and ground in a ball mill. Thereafter, particles of 40 microns and larger are screened off.

The resulting powder is mixed at a volume ratio of 4:1 with the above described unsintered calcium aluminum fluorosilicate glass powder previously depleted in calcium at the surface by treatment with 0.1% hydrochloric acid, as described in U.S. Pat. No. 4,376,835.

The resulting dental material is mixed at a weight ratio of 5:1 with a solution of 37 grams of a copolymer (1:1) of acrylic acid and maleic acid, 9 grams of tartaric acid and 54 grams of water. The thereby obtained cement mixture can be processed within about 3 minutes and hardens in about 8 minutes.

A molar filling made from this cement has a glossy golden surface; after having been in the mouth for 3 years it does not show any visible wear. Surface gloss and color have even slightly improved as compared with the initial state.

EXAMPLE 2

Silver-Containing Sintered Powder 17.5 parts by weight of calcium aluminum fluorosilicate glass powder corresponding to the composition B in Table I (average particle size, 6 microns) are homogeneously blended with 82.5 parts by weight of a finely divided silver powder (silver powder II F of Messrs. Degussa, average particle size 3.5 microns, 99.9% Ag) and processed as described in Example 1 by molding, sintering, grinding and mixing with the same untreated calcium aluminum fluorosilicate glass powder to form a powdered dental material.

After processing as described in Example 1, tooth fillings are made in the molar region. The fillings have a metallic gray gloss which has darkened only slightly after an observation period of 2 years; the fillings do not show any wear.

Comparative Test

In several test persons, fillings were placed in the molar region which were based on the following cement powders:
  (a) gold-contaning dental material of the invention as described in Example 1;
  (b) silver-containing dental material of the invention as described in Example 2;
  (c) glass ionomer cement powder according to Example 1 of U.S. Pat. No. 4,376,835;
  (d) a powder composed according to (a) which, however, had not been subjected to a sintering treatment.

After two years in the test persons' mouths, the fillings were examined and showed the following results:
  (a) intact glossy golden surface, no visible wear;
  (b) intact glossy, slightly darker surface, no visible wear;
  (c) slightly rough surface, defects by breakage in the edge regions,
  (d) rough surface with visible abrasion, breakage in the edge regions.

From these results, it is clear that the dental material of the present invention provides improved results over glass ionomer cement powders which have not been sintered or subjected to a thermal treatment.

The invention being thus described, it will be obvious that the same may be varied in many ways. Such variations are not to be considered as a departure from the spirit and scope of the invention, and all such modifications as would be obvious to one skilled in the art are intended to be included within the scope of the following claims.

We claim:

1. A powdered dental material composition comprising (a) calcium aluminum fluorosilicate glass and (b) a member selected from the group consisting of precious metals suitable for dental use and alloys of said precious metals with one another and/or with up to 40% by weight of non-precious metals, based on the weight of the alloy, at least a portion of the component (a) being in the form of a sintered mixture with the component (b).

2. A powdered dental material composition according to claim 1, further including a polycarboxylic acid and/or a chelating agent, each in powdered form.

3. A powdered dental material composition according to claim 1, wherein unsintered calcium aluminum fluorosilicate glass powder depleted in calcium at the surface thereof, the quotient of the atomic ratio Si/Ca at the powder particle surface and the atomic ratio Si/Ca in the core region being at least 2.0, is present in admixture with the powdered metal-containing sintered dental material.

4. A powdered dental material composition according to claim 3, wherein said quotient is at least 3.0.

5. A powdered dental material composition according to claim 1, wherein the average weight average particle size ranges from 1 to 20 microns.

6. A powdered dental material composition according to claim 5, wherein the average weight average particle size ranges from 3 to 10 microns.

7. A powdered dental material composition according to claim 1, wherein the precious metal is gold, platinum, palladium or silver.

8. A powdered dental material composition according to claim 7, wherein the non-precious metal is copper, tin, indium or zinc.

9. A powdered dental material composition according to claim 2, wherein the polycarboxylic acid is polymaleic acid, polyacrylic acid, maleic acid/acrylic acid copolymers, acrylic acid/itaconic acid copolymers or mixtures thereof.

10. A powdered dental material composition according to claim 2, wherein the chelating agent is tartaric acid.

11. A process for preparing a powdered dental material composition according to claim 1 which comprises mixing a powder of (a) calcium aluminum fluorosilicate glass and (b) a member selected from the group consisting of precious metals suitable for dental use and alloys of said precious metals with one another and/or with up to 40% by weight of non-precious metals, based on the weight of the alloy, sintering the resulting mixture at a temperature in excess of 600° C., and grinding the sintered product to form a powder.

12. A process according to claim 11, wherein the mixture of component (a) and component (b) is molded into a shaped structure prior to sintering.

13. A process according to claim 11, wherein the sintered powder is mixed with unsintered calcium aluminum fluorosilicate glass, at least one polycarboxylic acid and/or a chelating agent, each in powdered form.

14. A process according to claim 11, wherein the proportion of component (b) is from 20% to 80% by volume of the mixture of components (a) and (b).

15. A process according to claim 11, wherein the sintering is carried out in a vacuum of less than 10 mbar.

16. A process according to claim 11, wherein the precious metal is silver or gold and the sintering is carried out at a temperature less than the melting point thereof.

17. A process according to claim 13, wherein unsintered calcium aluminum fluorosilicate glass powder is mixed with the sintered powder, said unsintered glass powder being depleted in calcium at the surface thereof, the quotient of the atomic ratio Si/Ca at the powder particle surface and the atomic ratio Si/Ca in the core region being at least 2.0.

18. A self-hardening glass ionomer dental cement or filling material comprising the dental material composition of claim 2 and water.

19. A method of filling teeth or for cementing dental crowns and bridges which comprises applying the glass ionomer dental filling material or cement of claim 18 as the filling material or fixing cement to the teeth to be treated.

* * * * *